(12) United States Patent
Cerofolini

(10) Patent No.: US 8,911,376 B2
(45) Date of Patent: Dec. 16, 2014

(54) ARRAY OF ELECTROACOUSTIC TRANSDUCERS AND ELECTRONIC PROBE FOR THREE-DIMENSIONAL IMAGING

(75) Inventor: Marino Cerofolini, Subbiano (IT)

(73) Assignee: Esaote, S.p.A., Genova (IT)

( * ) Notice: Subject to any disclaimer, the term of this patent is extended or adjusted under 35 U.S.C. 154(b) by 530 days.

(21) Appl. No.: 12/763,256

(22) Filed: Apr. 20, 2010

(65) Prior Publication Data

US 2010/0274136 A1 Oct. 28, 2010

(30) Foreign Application Priority Data

Apr. 23, 2009 (EP) .................................... 09425155

(51) Int. Cl.
*A61B 8/14* (2006.01)
*B06B 1/06* (2006.01)
*H01L 41/053* (2006.01)
*H01L 41/047* (2006.01)

(52) U.S. Cl.
CPC ................ *B06B 1/0622* (2013.01); *A61B 8/14* (2013.01); *H01L 41/053* (2013.01); *B06B 1/06* (2013.01); *H01L 41/047* (2013.01)
USPC ............................ 600/459; 600/437; 600/443

(58) Field of Classification Search
CPC .......... A61B 8/14; B06B 1/0622; B06B 1/06; H01L 41/053; H01L 41/047
USPC ............................ 600/437–459; 156/154, 268
See application file for complete search history.

(56) References Cited

U.S. PATENT DOCUMENTS

| | | | | |
|---|---|---|---|---|
| 4,893,624 A | * | 1/1990 | Lele | .................................. 601/3 |
| 5,893,832 A | * | 4/1999 | Song | ............................. 600/443 |
| 5,911,692 A | * | 6/1999 | Hussain et al. | ............... 600/447 |
| 6,483,225 B1 | | 11/2002 | Spigelmyer | |
| 2002/0139193 A1 | * | 10/2002 | Angelsen et al. | ............... 73/602 |
| 2004/0068191 A1 | | 4/2004 | Seward | |
| 2006/0074314 A1 | * | 4/2006 | Slayton et al. | ............... 600/439 |
| 2012/0059288 A1 | * | 3/2012 | Barthe et al. | ...................... 601/2 |

FOREIGN PATENT DOCUMENTS

EP 1348954 A1 10/2003

OTHER PUBLICATIONS

European Search Report for Application No. 09425155.0 dated Sep. 6, 2010.

* cited by examiner

*Primary Examiner* — Vani Gupta
(74) *Attorney, Agent, or Firm* — Woodard Emhardt Moriarty McNett & Henry, LLP

(57) ABSTRACT

An electroacoustic transducer assembly and probe for emitting and receiving acoustic radiation beams. The transducer assembly comprising an array of electroacoustic transducers composed of a plurality of individual transducer elements each one being composed of an electroacoustic element. A means for defocusing a radiation pulse emitted from the transducer element is associated with each transducer element. The defocusing means is constructed and arranged to cause the radiation pulse to generate a substantially cylindrical or spherical acoustic field.

29 Claims, 10 Drawing Sheets

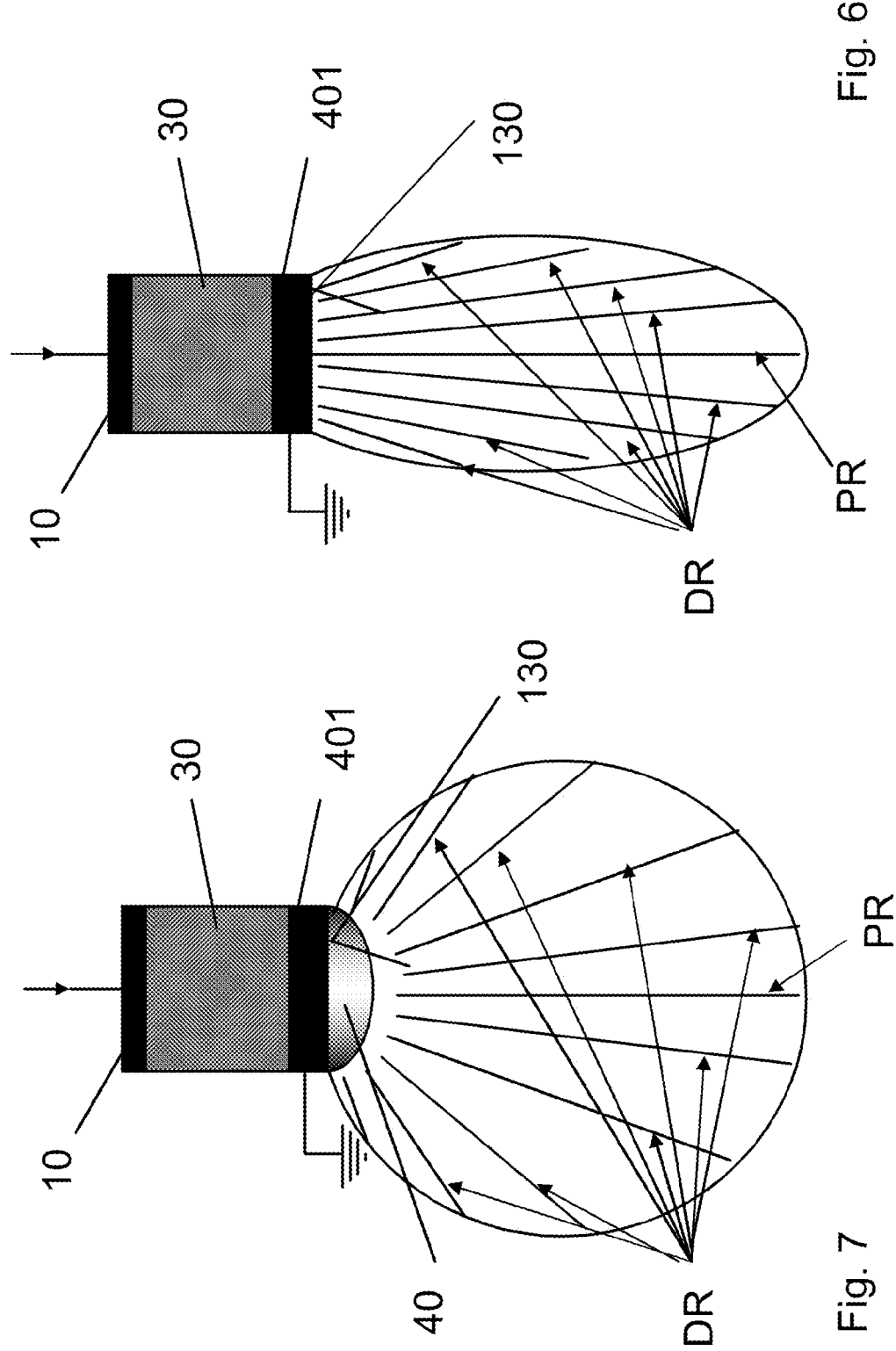

ARRAY OF ELECTROACOUSTIC TRANSDUCERS AND ELECTRONIC PROBE FOR THREE-DIMENSIONAL IMAGING

CROSS-REFERENCE TO RELATED APPLICATION

The present application claims the benefit of European Patent Application No. EP 09425155.0, filed on Apr. 23, 2009, which is hereby incorporated by reference in its entirety.

BACKGROUND

The present invention generally relates to the field of diagnostic imaging and, more specifically, to an array of electroacoustic transducers and an electronic probe for three-dimensional imaging.

Transducer arrays are widely used for making ultrasound probes and they are the device for generating acoustic radiation beams or the device for receiving acoustic signals and for transforming them into electric signals. Generally the same transducer array is used alternatively both for generating acoustic radiation beams to be transmitted and for receiving acoustic pulses to be converted into electric signals. However the arrangement with an ultrasound probe provided with two transducer arrays operating independently one of which for transmitting acoustic radiation beams and the other one for receiving acoustic pulses cannot be ruled out.

With regards to conventional ultrasound probes, for example, the transmitting/receiving head comprises a front side from which acoustic radiation ultrasound beams are emitted in a direction of propagation towards a body under examination and on which front side pulses reflected by the body under examination impinge. The head has a back side opposite to the front side and it is oriented towards the inside of the casing of the ultrasound probe and towards means for supporting said head inside the casing.

Acoustic radiation beams are composed of acoustic pulses emitted by the individual transducer elements that are combined together such to generate an acoustic radiation beam having a predetermined direction of propagation and a predetermined focusing along said direction of propagation.

The transmitting/receiving head generally comprises, with an order starting from the back side towards the front side and corresponding to the direction of propagation of acoustic waves, a first layer composed of an array of contact electrodes, having each one a separate electric connection line to an electric contact pin being a part of a multi-pin electric connector and provided at one peripheral edge of the layer of contact electrodes. The layer composed of the array of contact electrodes is superimposed by a further layer composed of an array of piezoelectric elements. These can be composed of ceramic elements and they constitute the individual transducers converting electric excitation signals into acoustic pulses emitted from one surface thereof and/or converting acoustic pulses impinging thereon into electric signals. Each one of the transducer elements of the array is coincident with a contact electrode and is electrically connected thereto for example by means of a simple surface contact of each individual contact electrode of a corresponding transducer element. The array of contact electrodes and of the overlapping piezoelectric elements is supported by an acoustically and electrically insulating material that can be a simple supporting layer and/or can incorporate at least partially the electrodes and the piezoelectric elements filling at least for a portion of the thickness of the overlapping contact electrodes and piezoelectric elements the gaps there between. A third layer is composed of a ground electrode. It can be in the form of a continuous sheet overlapped to the side of the array of piezoelectric elements opposite to the one overlapped by the contact electrodes. As an alternative said third layer can be made like contact electrodes by an array of individual elements which are electrically separated one from the other and each one overlapping and being electrically connected only to one of the piezoelectric elements.

Generally on the third grounding layer there are provided one or more layers of acoustic matching layers acting for matching the acoustic impedance of the transducers to the acoustic impedance of the operation environment, for example of the body under examination in this case using the transmitting/receiving head into an ultrasound probe.

As it is clear from what disclosed above, within the transducer array, each transducer has a predetermined surface from which the acoustic pulse is emitted/received and transducers have a predetermined distance one with respect to the other, while the transducer array in turn has a predetermined length and width depending on the fact it is composed of only one row of transducers or of several rows of transducers.

Characteristics of transducer arrays depend on different dimensional elements both regarding the overall size of the transducer array and regarding the size of the individual transducer elements.

The equation defining the position of the natural focus within a transducer having a length D (defined as the aperture of the transducer) is the following:

$$F = D^2/4\lambda \qquad (1)$$

where $\lambda$ is the wavelength.

Therefore, the greater the aperture is, the deeper is arranged the natural focus. The need of making transducers with apertures as wide as possible arising there from.

If the number of transducers in a transducer array is determined (for example 192) and if the maximum operating depth of the transducer array is determined (for example 4-5 cm), so the formula (1) defines the pitch, i.e. the length of each transducer (for example 0.2 mm).

Each transducer element in turn has a radiation pattern which tends to diverge, with respect to the axis perpendicular to the surface emitting/receiving acoustic pulses (direction of propagation or incidence of the acoustic pulses), by an angle θ such that:

$$\sin \theta = 0.6 \lambda/a \qquad (2)$$

where a denotes the radius of the transducer element (assuming it has a circular section).

With reference to the formula (2) it can be deduced that the larger the transducer element is, the less the radiation diverges and, therefore, the more the emitted radiation beam tends to be a tube with a diameter equal to the diameter of the transducer element. Vice versa, if the transducer element tends to approximate a point source so the emitted beam tends to become wider till theoretically taking a spherical radiation pattern.

Therefore if transducer elements of a transducer array emit in a very directional manner, that is they have a narrow radiation lobe in the direction orthogonal to the surface of the element emitting the acoustic radiation, so it is not easy or even it is impossible to combine individual acoustic pulses of the individual transducer elements such to achieve an overall acoustic pulse for the transducer array focused along a line of propagation which is deviated by a certain angle with respect to the line of propagation orthogonal to the emitting surface of the transducer array, i.e. it is impossible to steer the emitted acoustic radiation. Such action substantially is the same as electronically steered the beam such to bring the radiation lobe of each element to cover a direction offset by an angle with respect to the direction perpendicular to the surface emitting the acoustic radiation of each element. On the contrary if the radiation lobe is wide, spherical at a greatest extent, the emitted acoustic radiation has no preferential directions and so the emitted pulse can be used for any directions. Therefore, in addition to deviate the beam in any directions, all the transducer elements can give their contribution to the overall pulse focused on a predetermined focus point, thus increasing the focusing level and, therefore, improving the lateral resolution.

The above theory is described in more details in the following publication "Physics and Instrumentation of Diagnostic Medical Ultrasound" by Peter Fish, John Wiley & Sons, chapter 4, pages 27-49.

Obviously, if a linear probe is considered, wherein transducer elements are placed one near the other on only one row having a predetermined length, the transducer array will have an aperture corresponding to the length of said row. In such case transducer elements can have rectangular emitting surfaces with the shortest side parallel to the length of the row of adjacent transducer elements, the elements being arranged one near the other along the longest sides thereof and the longest sides of the transducer elements being provided as parallel to the width dimension of the row of transducers.

In this case, by reducing the size of the transducer elements in the direction parallel to the length of the row of the adjacent transducer elements, i.e. by making transducer elements more narrow, for each transducer element the acoustic field or the main lobe takes a cylindrical configuration and not a spherical configuration with the axis of the cylinder parallel to the length extension of the transducer element, that is in a direction parallel to the width dimension or of the longest side of the row of transducer elements. This can be applied also to probes with two-dimensional arrays comprising several rows of rectangular transducer elements such as described above.

Therefore in the present description and in the claims, when it is not expressly terminologically differentiated, the spherical or similar to spherical term is intended to also include a cylindrical or similar to cylindrical configuration, as a special condition wherein one of the angles is fixed expressed in polar variables.

In electronic probes for three-dimensional images, there is the need of having a wide surface of the transducer array forming the transmitting/receiving head in order to have a good beam focusing even at relatively deep depth.

A wide surface of the transducer array being desired, and at the same time the possibility of making high steering operations of the acoustic radiation beam being desired, the above theory provides the solution of a high number of very small transducer elements. However this requires a considerable increase of the number of lines connecting each transducer element to the unit generating the excitation electric signal and/or to the unit processing the electric signal corresponding to acoustic pulses received from each transducer element, obviously with major costs as well as with practical restrictions as regards the maximum number of transducer elements and so of channels due to the fact that each channel corresponds to a line that is constituted by a conductor of a multichannel cable. In addition to the above there is obviously also a rise of costs and of the complexity of the hardware generating excitation pulses for transducer elements and processing reception signals of individual transducer elements.

Therefore considering the fact of keeping a restricted number of transducer elements in combination with an increase of the overall dimension of the transducer array, two contrasting conditions would arise: the fact of keeping radiant surfaces of the individual transducer elements small would lead to a focusing loss at deep depths, while it would lead to high beam steering, and the fact of increasing the radiant surfaces of the individual transducer elements would lead to lose the possibility of making high steering, but it would lead to a good focusing at deep depth.

Therefore it is currently not possible to make transducer arrays having a restricted number of transducer elements and preferably having a typical number of transducer elements for conventional ultrasound apparatus and at the same time allowing high quality three-dimensional echographies to be achieved. For carrying out three-dimensional echographies it is necessary to use transducer arrays having a great number of transducers, and therefore it is necessary to provide both probes and ultrasound apparatuses specifically intended for said function.

Therefore, there is a need for an improved array of electroacoustic transducers and an electronic probe for three-dimensional imaging.

SUMMARY

The present disclosure provides an improved electroacoustic transducer array and electronic probe. The claims, and only the claims, define the invention.

The present disclosure aims at providing a transducer array for emitting/receiving acoustic radiation beams, that, with a restricted number of transducer elements, particularly a small number of transducers such as the one typically used in two-dimensional imaging probes in conventional ultrasound apparatuses, allows three-dimensional echographies to be carried out with a deep focusing depth of the acoustic radiation beam and at the same time keeping the possibility of making high steering of said acoustic radiation beam.

Moreover the present disclosure aims at providing an ultrasound probe having a low number of transducer elements, with a high focusing depth and high steering to be used in combination with conventional two-dimensional imaging ultrasound apparatuses and in order to achieve three-dimensional ultrasound images by means of said combination.

According to some embodiments of the present disclosure, above-identified drawbacks are overcome by providing a transducer array of the type described hereinabove with means for defocusing the radiation beam or pulse emitted from the transducer element are associated to each transducer element of the transducer array such that said pulse generates a cylindrical or spherical acoustic field or as much similar as possible to a cylindrical or spherical acoustic field.

According to a one embodiment, each transducer element at the side emitting acoustic pulses is provided with an element defocusing the pulse emitted by the transducer element which defocusing element modifies the acoustic field such that said pulse generates a cylindrical or spherical acoustic field or as much similar as possible to a cylindrical or spherical acoustic field.

The defocusing element is composed of a layer overlapped to each transducer element having a convex shape at the side opposite to the one oriented towards the transducer element when said layer has a high velocity in propagating the acoustic radiation, while said defocusing element is composed of a layer overlapped to each transducer element having a concave shape at the side opposite to the one oriented towards the transducer element when said layer has a low velocity in propagating the acoustic radiation and depending on whether the acoustic field is cylindrical or spherical it has a curvature according to only one axis or according two axes perpendicular one to the other.

An additional embodiment provides each transducer element to be in turn divided into two, three or more sections which are acoustically and/or electrically insulated there being provided means for feeding the excitation signal to each individual section of the transducer with a predetermined time delay for the different sections constituting the transducer relative to each other and according to an excitation order defined by a predetermined time sequence and means for combining the components of the electric reception signal of the transducer element generated by the individual sections thereof each one with a predetermined delay than the other components of the other sections according to an order defined by a predetermined time sequence for combining the components of the reception signal of the individual sections.

When the individual transducer elements are rectangular and particularly when making linear arrays of transducer elements, i.e. composed of a single row of adjacent transducer elements that are arranged side by side along the longest sides thereof, while the shortest side of the transducer elements is parallel to the length extension of said transducer row, said transducer elements are divided into sections composed of two, three or more rectangular elements having a narrower side equal to a portion of the overall length of the shortest side of the transducer element, and which sections are electrically and/or acoustically insulated one with respect to the other the electric excitation signal for generating the acoustic radiation beam being provided to each one of the two, three or more sections of the transducer element with a predetermined delay than the other sections of the same transducer element feeding delays of the excitation signal being determined such to generate a cylindrical acoustic field or an acoustic field as much similar as possible to a cylindrical acoustic field.

A further embodiment provides sections of the individual transducers to have a concentric shape and to be electrically and/or acoustically insulated one with respect to the other, the electric excitation signal for generating the acoustic radiation beam being provided to each one of the two, three or more concentric sections of the transducer element with a predetermined delay for each one of said concentric sections than the other concentric sections of the same transducer element and feeding delays of the excitation signal being determined such to generate a spherical acoustic field or an acoustic field as much similar as possible to a spherical acoustic field.

In this case, the time sequence for exciting the adjacent or concentric sections of each one of the transducer elements is such that the central section is the first to be excited and then adjacent or annular sections which are progressively more external or distant from the central one are sequentially excited.

For the application of the delays, it is possible to provide delay inductances put in series between the input of the excitation signal and the corresponding rectangular or concentric section of the transducer element.

With regards to the construction, with reference to the array of transducer elements where each transducer element comprises at least a contact electrode, it is possible to provide the transducer element to be composed of sections separated from one another each one overlaps under electric contact a congruent section of the contact electrode which is composed of sections too, while each section of the contact electrode is electrically connected to the adjacent one by an inductance and the input line for the excitation signal is connected to the central section or to the innermost section.

With regards to the reception signals, the same construction is applied. In this, case delays defined by inductances provided between individual sections of each transducer element act on the components of the reception signal which are generated by the acoustic pulse impinging on each one of said sections of the transducer element.

The present disclosure also provides an ultrasound probe comprising a casing wherein an head transmitting/receiving acoustic radiation beams or pulses is housed which transmitting/receiving head comprises an array of transducers and which transducer array comprises a predetermined number of individual transducer elements, each transducer element being associated to an electrode for the input/output of an electric signal exciting the transducer element corresponding to the emission of an acoustic signal or an electric reception signal corresponding to an acoustic signal impinging on the corresponding transducer element respectively, each electrode being in turn connected to a dedicated transmission line for the electric excitation signal or the electric reception signal respectively and moreover each transducer element being connected to a ground electrode and said piezoelectric elements being supported by an array made of an acoustically and electrically insulating material wherein they are at least partially embedded and wherein for each transducer element of the array of transducer there are associated means for defocusing the radiation beam or pulse emitted there from such that said pulse generates a cylindrical or spherical acoustic field or an acoustic field as much similar as possible to a cylindrical or spherical acoustic field.

According to one embodiment, each transducer element of the transducer array is provided at the side emitting acoustic pulses with an element defocusing the pulse emitted by the transducer element such that said pulse generates a cylindrical or spherical acoustic field or an acoustic field as much similar as possible to a cylindrical or spherical acoustic field.

The defocusing element is composed of a layer laid on each transducer element having a convex shape at the side opposite to the side oriented towards the transducer element when said layer has a high velocity in propagating the acoustic radiation, while said defocusing means is composed of a layer laid on each transducer element having a concave shape at the side opposite to the side oriented towards the transducer element when said layer has a low velocity in propagating the acoustic radiation, said curvature being provided only according to one axis or according to two axes orthogonal one another.

Another embodiment of the present disclosure provides an ultrasound probe comprising a casing wherein a head for transmitting/receiving acoustic radiation beams or pulses is housed which transmitting/receiving head comprises an array of transducers and which transducer array comprises a predetermined number of individual transducer elements, each transducer element being associated to an electrode for the input/output of an electric signal exciting the transducer element corresponding to the emission of an acoustic signal or an electric reception signal corresponding to an acoustic signal impinging on the corresponding transducer element respectively, each electrode being in turn connected to a dedicated transmission line for the electric excitation signal or the electric reception signal respectively and moreover each transducer element being connected to a ground electrode and said piezoelectric elements being supported by an array made of an acoustically and electrically insulating material wherein they are at least partially embedded and wherein each transducer element is in turn divided into two, three or more sections which are acoustically and/or electrically insulated one with respect to the other there being provided means for feeding the excitation signal to each individual section of the transducer with a predetermined time delay for the different sections constituting the transducer one with respect to the other and according to an excitation order defined by a predetermined time sequence and means for combining the components of the electric reception signal of the transducer element generated by the individual sections thereof each one with a predetermined delay than the components of the other sections according to an order defined by a predetermined time sequence for combining the components of the reception signal of the individual sections.

When the individual transducer elements are rectangular and particularly when making linear arrays of transducer elements, i.e. composed of a single row of adjacent transducer elements that are arranged side by side along the longest sides thereof, while the shortest side of the transducer elements is parallel to the length extension of said transducer row, the transducer elements are divided into sections composed of two, three or more rectangular elements having a narrower side equal to a portion of the overall length of the shortest side of the transducer element, and which sections are electrically and/or acoustically insulated one with respect to the other the electric excitation signal for generating the acoustic radiation beam being provided to each one of the two, three or more sections of the transducer element with a predetermined delay than the other sections of the same transducer element feeding delays of the excitation signal being determined such to generate a cylindrical acoustic field or an acoustic field as much similar as possible to a cylindrical acoustic field.

A further embodiment provides the sections of the individual transducers to have a concentric shape and to be electrically and/or acoustically insulated one with respect to the other the electric excitation signal for generating the acoustic radiation beam being provided to each one of the two, three or more concentric sections of the transducer element with a predetermined delay for each one of said concentric section than the other concentric sections of the same transducer element and feeding delays of the excitation signal being determined such to generate a spherical acoustic field or an acoustic field as much similar as possible to a spherical field.

In this case, the time sequence for exciting the adjacent or concentric sections of each transducer element is such that the central section is the first to be excited and then adjacent or annular sections which are progressively more external or distant from the central one are sequentially excited.

For the application of the delays it is possible to provide delay inductances put in series between the input of the excitation signal and the corresponding rectangular or concentric section of the transducer element.

Regarding the construction, with reference to the array of transducer elements where each transducer element comprises at least a contact electrode, it is possible to provide the transducer element to be composed of sections separated from one another each one overlaps under electric contact a congruent section of the contact electrode which is composed of sections too, while each section of the contact electrode is electrically connected to the adjacent one by an inductance and the input line for the excitation signal is connected to the central section or to the innermost section.

Regarding the reception signals, the same construction is applied, in this case delays defined by inductances provided between individual sections of each transducer element act on the components of the reception signal which are generated by the acoustic pulse impinging on each one of said sections of the transducer element.

According to one embodiment, each concentric section of the contact electrode of each transducer element is connected by a conductive track on a board supporting the transducer array to a corresponding contact pin of a termination for connecting the transmitting/receiving head to the multi-channel cable for the connection to the ultrasound apparatus and/or to a preventive processing electronics whose output is in turn connected to the multi-channel cable for the connection to the ultrasound apparatus. In this case, inductances can be provided on the board supporting the transducer array between tracks connecting sections of the electrodes of each transducer element or within the multi-pin connector where pins for the connection to the multi-channel cable are provided or in the preventive processing circuitry for electric signals in case provided into the ultrasound probe.

From the above, it is clear that by means of relatively simple and inexpensive arrangements, the present disclosure makes it possible to make transducer arrays and ultrasound probes with a restricted number of transducers and having great dimensions, keeping the surface of the individual transducer elements wide and at the same time guaranteeing the acoustic field generated by each transducer element to be spherical or as much similar as possible to a spherical one for guaranteeing a high steering.

Thanks to the above, contrasting technical effects have been met without considering losses in the sensitivity, reduction in the focusing effect and possibilities of high steering. Therefore the field wherein conventional ultrasound apparatuses are used has been widened allowing even these apparatuses to be used for high quality three-dimensional echographies.

A further embodiment can provide a combination of the two alternative solutions, wherein defocusing means as acoustic lens are provided and wherein the individual transducer elements are further divided into sections that are excited with a delay one with respect to the other and/or wherein the components of the reception signal which are generated from each section are summed into the reception signal with a predetermined delay one with respect to the other.

Further improvements are the subject of the dependent claims.

The characteristics of the invention and the advantages derived there from will be more apparent from the following description of the non-limiting embodiments and as illustrated in the drawings.

BRIEF DESCRIPTION OF THE DRAWINGS

FIGS. 6 and 7 are schematic views showing only approximately the acoustic field generated from a transducer element having an extension of the emitting/receiving surface that is not an approximation of a point source without defocusing means and with defocusing means respectively.

DESCRIPTION OF THE SELECTED EMBODIMENTS

Figure 1:
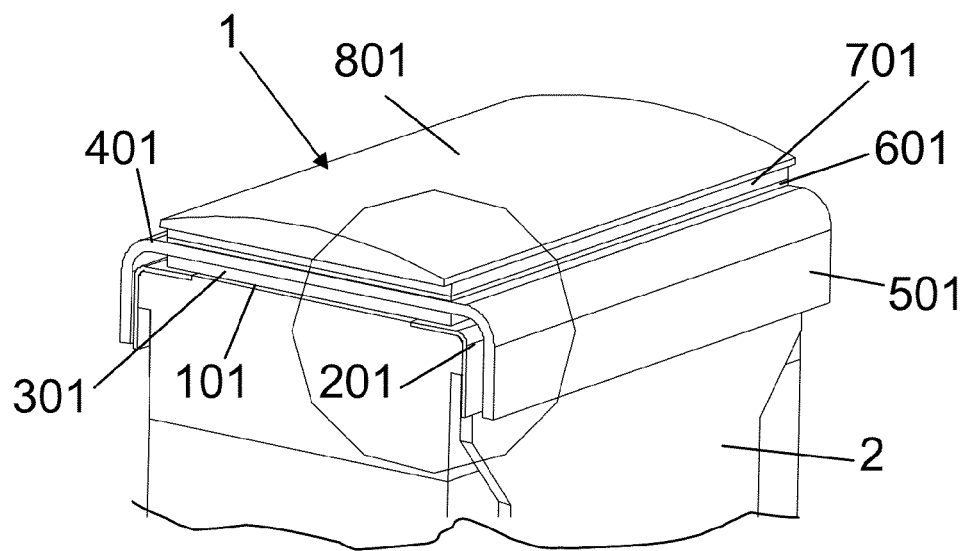
FIG. 1 is a perspective view of a head transmitting/receiving acoustic radiation pulses or beams within a conventional ultrasound probe according to the prior art.

For the purpose of promoting an understanding of the principles of the invention, reference will now be made to the embodiments illustrated in the drawings and specific language will be used to describe the same. It will nevertheless be understood that no limitation of the scope of the invention is thereby intended. Any alterations and further modifications in the described embodiments, and any further applications of the principles of the invention as described herein are contemplated as would normally occur to one skilled in the art to which the invention relates. One embodiment of the invention is shown in great detail, although it will be apparent to those skilled in the relevant art that some features that are not relevant to the present invention may not be shown for the sake of clarity.

The language used in the claims is to only have its plain and ordinary meaning, except as may be explicitly defined herein. Such plain and ordinary meaning is inclusive of all consistent dictionary definitions from the most recently published Webster's dictionaries and Random House dictionaries.

Figure 2:
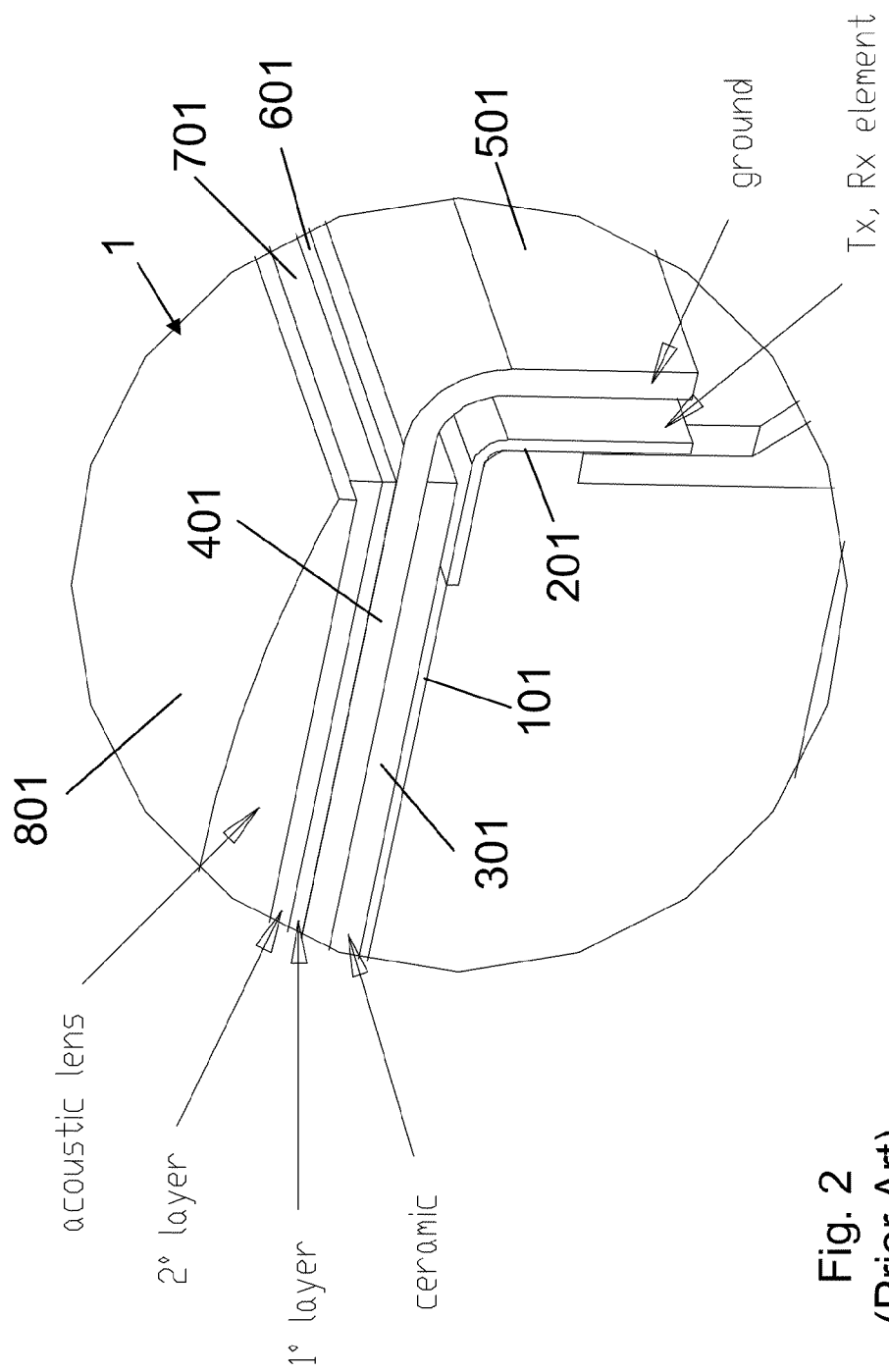
FIG. 2 is an enlarged view of the probe of FIG. 1.
Figure 3:
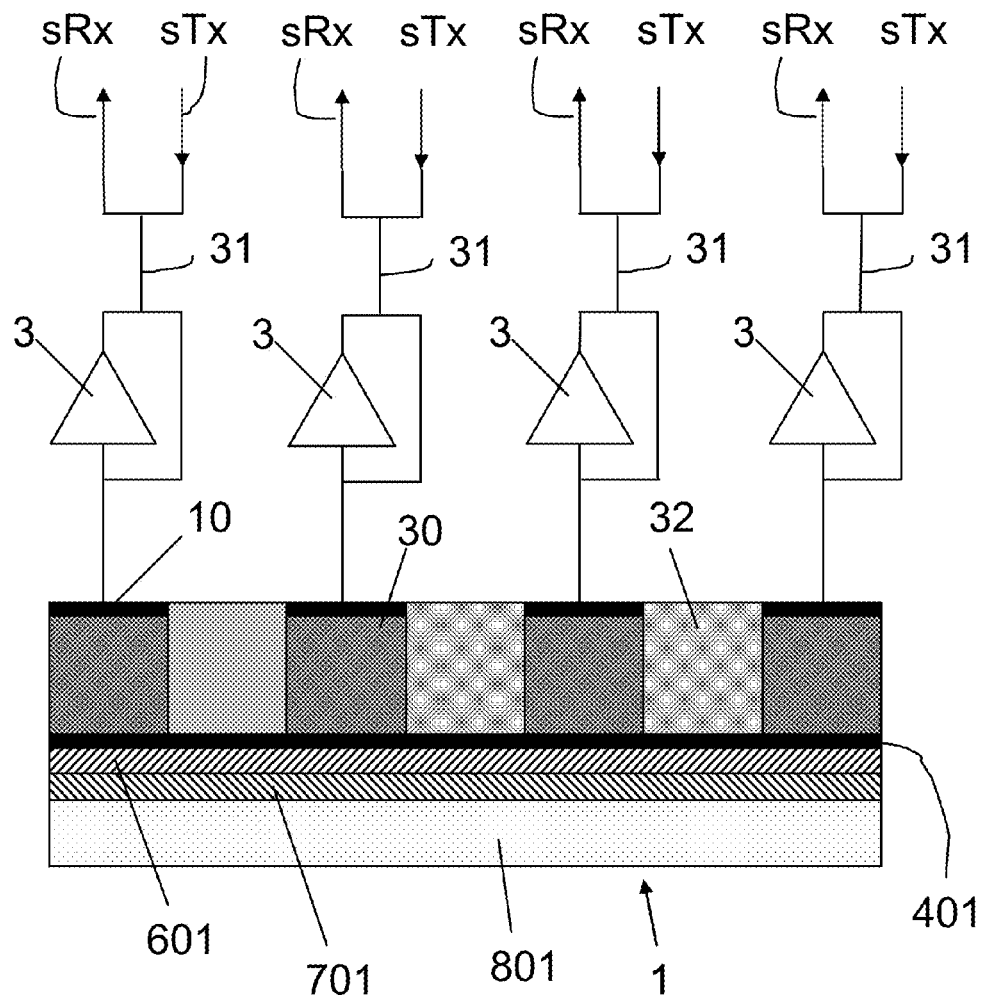
FIG. 3 is a schematic view showing the principle according to which the transmitting/receiving head is made, that is the transducer array within the ultrasound probe of FIG. 1, with reference to some transducer elements.

With reference to FIGS. 1 to 3, a conventional ultrasound probe is shown therein. These types of probes have a head for transmitting/receiving acoustic radiation beams or pulses comprising a transducer array composed of a restricted number of transducers. Generally the transducer array comprises 192 transducers. The latter may be arranged in a row, such as for the so called linear probes, or in two or more rows, such as for volumetric probes. Transducer elements are arranged side by side with their surfaces emitting/receiving the acoustic radiation aligned in the same plane which is the front side of the transducer array and said emitting/receiving surfaces have a predetermined shape and a predetermined extension and the individual transducer elements are spaced apart at a predetermined extent. The length dimension of the row of transducers of a linear probe is the so called aperture of the transducer array affecting the possibility of focusing an acoustic radiation beam composed of the components of the acoustic signal of the individual transducer elements up to a certain penetration depth of said beam into the body under examination. The surface of the transducer elements determines the shape of the acoustic field of the emitted acoustic radiation and therefore it affects the presence of components of the acoustic signal that is the acoustic field for directions of propagation different from the one perpendicular to the emitting/receiving surface of each individual transducer element. A greater or smaller distribution of the emitted acoustic radiation in directions different from the one perpendicular to the emitting/receiving surface of each transducer element affects both the possibility of deflecting the acoustic radiation beam of the transducer array in directions of propagation different from the one perpendicular to the front side of the transducer array, and the focusing capability that is the capability in concentrating the acoustic beam for a better lateral resolution. The surface of the emitting/receiving side of the individual transducer elements affects also the sensitivity of the transducer array as regards acoustic pulses impinging against the transducer array. As described in the Background in more detail, the above characteristics are contrasting requirements when manufacturing transducer arrays particularly for ultrasound probes.

The conventional probe of FIGS. 1 to 3, comprises a head 1 emitting/receiving acoustic radiation beams or pulses which has a front side from which the ultrasound beams or pulses are emitted in a direction towards the body under examination and the acoustic radiation pulses and/or beams reflected from the body under examination to the probe fall on such front side. The emitting/receiving head 1 has a back side which is opposite to the front side and which is oriented towards the inside of the probe casing.

The emitting/receiving head comprises an array of transducer elements arranged side by side according to one or more perpendicular directions such to form only one row of transducer elements arranged side by side or various adjacent rows of transducer elements arranged side by side respectively.

The array of transducer elements is composed of three layers that in an order starting from the back side towards the front side of the emitting/receiving head 1 are composed of a first layer 101 composed of an array of contact electrodes. Each contact electrode of the array 101 of contact electrodes has a separate electric connection line to a corresponding contact pin of a contact termination that may be provided along at least one peripheral edge of the layer of contact electrodes and which contact termination is indicated with 201.

On the layer composed of the array 101 of contact electrodes, a layer 301 composed of an array of transducer elements, particularly piezoelectric elements such as for example ceramic elements is laid. Each one of the transducer elements forms an emitting and/or receiving transducer element. Each one of the individual transducer elements is coincident and in electric contact with a corresponding contact electrode of the array 101 of contact electrodes. Particularly, each contact electrode is substantially congruent with the contact surface of the transducer element of the array 301 of transducer elements. A further layer overlapping the front side of the array 301 of transducer elements and so the front side thereof from which acoustic radiation beams or pulses are emitted and received, is composed of a single ground electrode 401 in electric contact with each one of the transducer elements of the array 301 of transducer elements. According to a variant embodiment the layer 401 may be in the form of an array of ground electrodes like the configuration of the array 101 of contact electrodes. Similarly to what described for the array 101 of contact electrodes, even with the continuous layer 401 constituting the common ground electrode or with said layer 401 composed of an array of electrically separated ground electrodes overlapped and congruent each one with one of the transducer elements, at a peripheral side of said layer 401 there is provided a contact termination 501 for the grounding connection.

Generally the layer 401 in the form of a common ground electrode or in the form of an array of ground electrodes is overlapped by one, two or more acoustic impedance matching layers denoted by 601 and 701. These two layers have the function of matching the acoustic impedance of the transducer array to the acoustic impedance of the body under examination acoustic radiation pulses or beams being transmitted thereto or reflected acoustic radiation pulses or beams being received there from.

As a last element on the second acoustic impedance matching layer 701 an acoustic lens 801 is provided which forms the interface between the emitting/receiving head 1 and the surface of the body under examination.

The electric connector terminations 201 and 501 of the array 101 of contact electrodes and of the ground layer 401 respectively are electrically and mechanically connected to a printed circuit board 2 which is provided with the necessary conductive tracks. The latter are in turn connected to a multi-channel cable for the connection of the probe to an ultrasound apparatus such as for example an ultrasound diagnostic imaging apparatus.

As depicted in FIG. 3, the individual elements indicated by 30 which form the transducer elements of the array 301 are, for example, piezoelectric elements connected each one to the units of the ultrasound apparatus by means of a line 31. The connection line 31 that is separated for each transducer element is connected to the contact electrode 10 of each corresponding transducer element and it acts both for feeding the excitation signal STX of the piezoelectric element to the transducer for exciting said piezoelectric element 30 to emit a corresponding acoustic pulse or an acoustic radiation beam and for transmitting to processing units of the ultrasound apparatus reception electric signals SRX generated by the corresponding piezoelectric element 30 when an acoustic pulse or an acoustic radiation beam impinges thereon. Therefore the same connection line 31 connects alternatively a corresponding transducer element to the units generating excitation signals STX and to the units processing the received signals SRX.

Since the cable connecting the probe to the ultrasound apparatus is a multi-channel cable having a separate conductor for each transducer element 30 of the array 301 of transducer elements, the cable has a certain capacitance and the reception signals generated by the transducer elements do not have enough power to overcome the capacitance of the cable, in order to increase the sensitivity and the pass band each connection line 31 has a preamplifier 3. In order to allow preamplifiers 3 to properly operate only on reception signals and not on excitation signals, the preamplifiers are provided with relatively complex decoupling circuits. The latter avoids the output of the preamplifier into the corresponding connection line 31 to be short-circuited with the input of the preamplifier during feeding of the excitation signals.

Moreover as it results from FIG. 3, each piezoelectric element, i.e. each transducer element 30, is separated from the adjacent one by a predetermined distance. The array of transducer elements at gaps between transducer elements being filled with a supporting or mutual bonding material denoted by 32, said material being an acoustically and/or electrically insulating material.

Moreover it is noted that in the shown conventional probe the same transducer elements used for emitting acoustic radiation beams or pulses are used also for receiving acoustic radiation pulses and/or beams. However according to the prior art there are also probes with two arrays of transducer elements one of which is intended only for emitting the acoustic radiation, while the other one is intended only for receiving the acoustic radiation.

As regards the construction said arrays can be provided as a single array of transducer elements, a portion thereof being connected only to the units generating the reception signals, while the remaining transducers are connected only to the units processing reception signals.

As it will be clear in the following description, the invention can be applied without distinction to both the two above variants, all the more so because with reference to the second variant provided with two transducer arrays one of which for the emission and the other for the reception, the fact that said two arrays are composed of a partial number of different transducer elements of a common array allows the inventive teaching to be applied to both the two variants substantially in the same way.

In order to make transducer arrays having a wide aperture for obtaining acoustic radiation beams focused up to deep propagation depths within the body under examination, surfaces emitting/receiving the acoustic radiation pulses or beams of the individual transducers being kept wide and so without losses of sensitivity and at the same time allowing the beam generated by the transducer array to have wide steering angles, the present disclosure provides means for defocusing the acoustic radiation pulses or beams emitted/received from each transducer element to be associated to each transducer element, which defocusing means act for generating an acoustic field of the transducer that is spherical or as much similar as possible to a spherical acoustic field.

Such an arrangement can be achieved in several ways.

Figure 4:
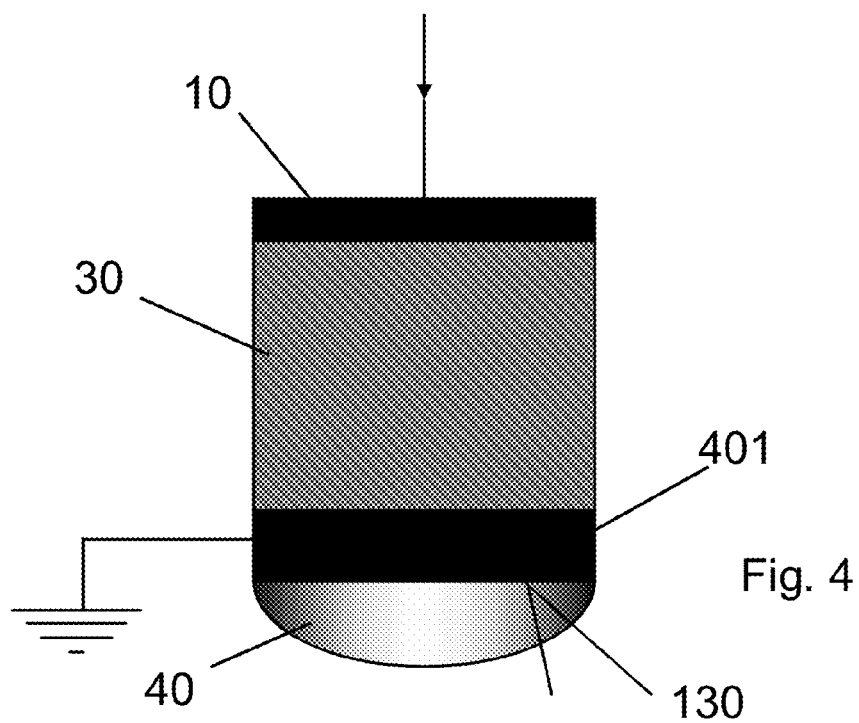
FIGS. 4 and 5 are schematic views of a transducer element and an array of transducer elements respectively provided with defocusing means in the form of convex acoustic lenses made of a material having a high sound propagation velocity.

FIG. 4 shows a transducer element according to one embodiment of the present disclosure. Similarly to what described above, each transducer element is composed of a piezoelectric element 30 which is electrically connected at the back side, i.e. at the side opposite to the emitting/receiving side, to a contact electrode 10 and at the front side, i.e. at the emitting/receiving side, to a ground electrode 401. While at the front side an acoustic lens made of a high velocity material is laid on the piezoelectric element, i.e. a material wherein the sound propagation velocity is high, and it is denoted by 40.

By means of such defocusing acoustic lens, the acoustic radiation emitted by a transducer element having a certain area of the emitting/receiving surface that is relatively wide than the approximation of a point receiving antenna or source, and that as such it would generate acoustic pulses focused almost only in the direction of propagation, i.e. perpendicularly to said emitting/receiving surface, diverges by providing acoustic signal components also in directions different than the perpendicular direction of propagation defined above. This allows the acoustic radiation beam generated by the transducer array to be steered, since each transducer has components of the acoustic pulse propagating according to different directions and by simply applying different delays to the excitation signals of the individual transducer elements it is possible to generate acoustic radiation beams focused according to directions different than the one perpendicular to the surface of the array of transducer elements, electronically imitating an inclination of the probe in said direction.

Figure 5:
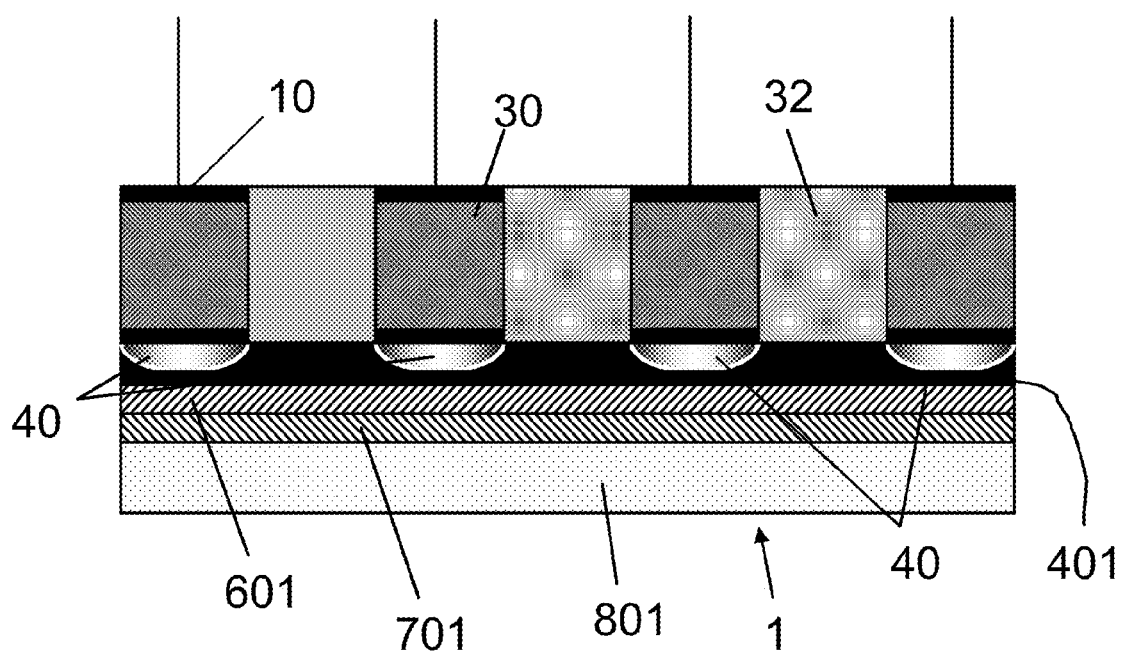

FIG. 5 depicts a portion of said array with a section according to a plane perpendicular to the surface of the transducer array.

FIG. 6 shows the acoustic field generated by a transducer element 30 without any defocusing means, when the area of the emitting surface 130 of the transducer element has such a size that it cannot be considered as an approximation of a point source. As it can be seen, the acoustic field with reference to the main emitting lobe is narrow and the signal components have directions of propagation DR with relatively small steering angles with respect to the direction of propagation PR according to the axis perpendicular to the emitting surface 130 of the transducer element 30.

FIG. 7 shows the same transducer element as in FIG. 6 but in this case there are provided defocusing means 40 on the emitting/receiving surface. Now the acoustic field is spherical or similar to a spherical field and signal components have directions of propagation DR whose direction of propagation has relatively wide angles with respect to the direction of propagation PR perpendicular to the emitting/receiving surface of the transducer element.

Figure 8:
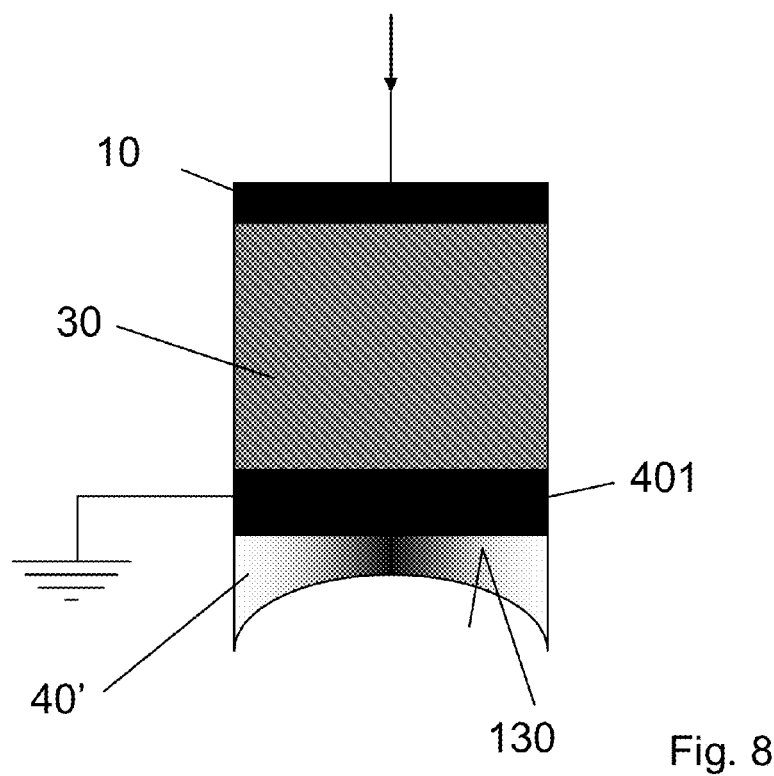
FIGS. 8 and 9 schematic views showing the embodiment where the defocusing means are composed of a material having a slow sound propagation velocity and wherein said defocusing means are concave acoustic lenses.
Figure 9:
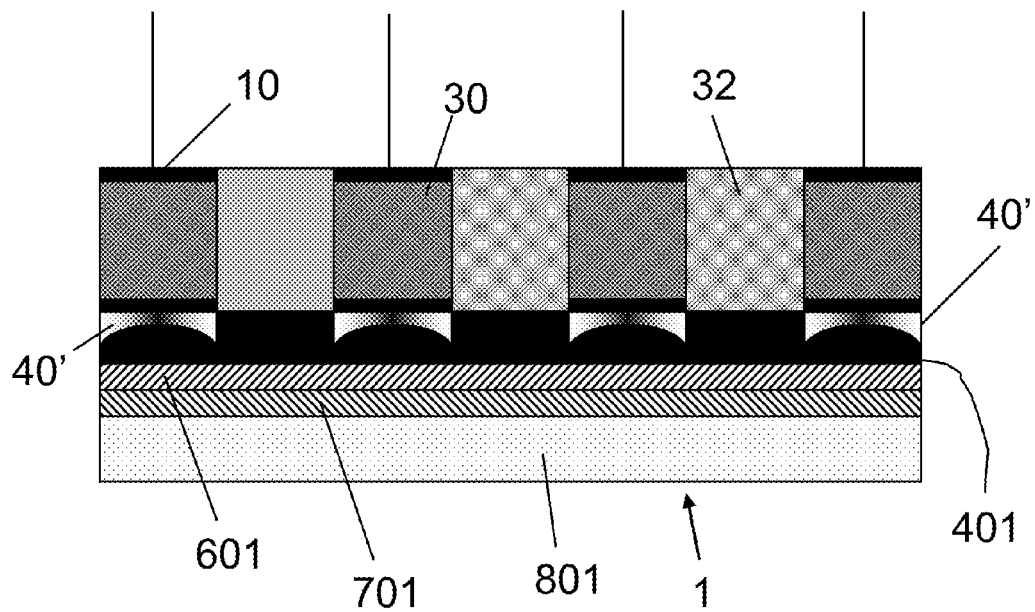

FIGS. 8 and 9 show a further embodiment of the present disclosure. In this case, defocusing means 40' are made of a material with a low sound propagation velocity and therefore defocusing means 40' are in the form of an acoustic lens which is concave at the front side, i.e. at the side from which the acoustic radiation is emitted.

Apart from that variation, the embodiment depicted. 8 and 9 is the same as the embodiment of FIGS. 4 and 5, with like parts being denoted by like reference numbers. Even the effect achieved on the shape of the acoustic field is the same as in FIGS. 6 and 7, so what has been disclosed in the figures is applicable also to the embodiment of FIGS. 6 and 7 by suitably replacing the convex element 40 with the concave element 40'.

Figure 10:
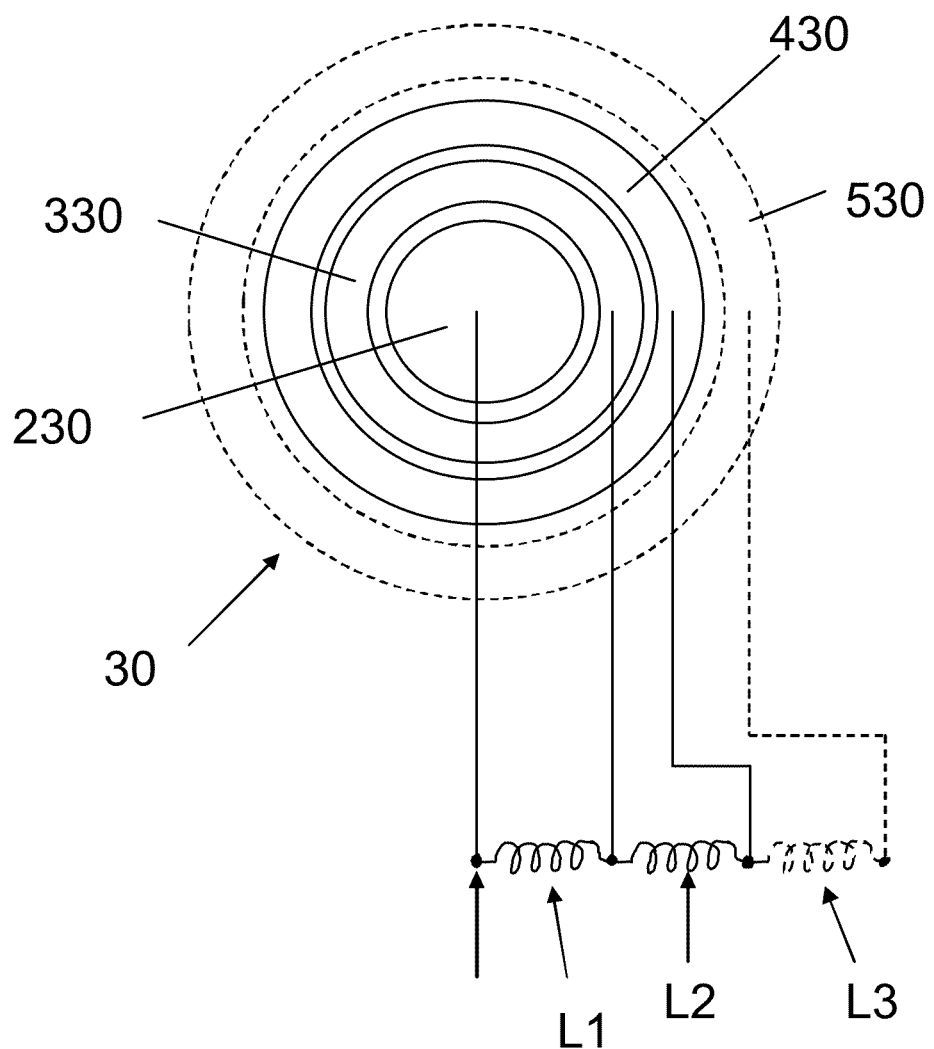
FIG. 10 is a schematic plan view of the transducer layer in which each transducer element of the transducer array is divided into concentric sub-elements and wherein transducer elements have a special circular shape that has not to be intended as a limitative one.

FIG. 10 shows a variant embodiment of the invention by a schematic plan view at the front side of the piezoelectric or transducer element.

In this case instead of providing defocusing means in the form of a kind of acoustic lens, the defocusing effect is achieved by a configuration of each transducer element 30 of the array 301 of transducer elements by dividing each transducer element into transducer element sections, each section being excited with a certain delay with respect to the adjacent section according to a predetermined order of the sequence for exciting the sections.

The sections are preferably composed of concentric transducer portions that are electrically and acoustically insulated one with respect to the other, the sections being spaced apart by gaps filled with the acoustically and/or electrically insulating material.

The concept is easy to understand in FIG. 10. In such example, each transducer is divided into a central plate 230 and into two further concentric rings 330, 430. As indicated by the ring 530 which is shown by broken line, theoretically there are no limitations to the number of concentric rings and so of sections which can be determined according to saving and effect principles and according to desired technical characteristics.

The sequence for feeding an excitation signal and similarly the delay sequence to be applied to the reception signal components one with respect to the other that have been generated by the different sections starts from the central plate 230 and then it sequentially involves the rings as they are more and more external. Therefore for example the excitation signal is firstly provided to the central plate 230, then with a certain predetermined delay to the ring 330 and so to the ring 430 and to the ring 530 if provided. Delays are calculated such that the global radiation field emitted by the transducer element, as the sum of the components of the individual sections is spherical or as much similar as possible to a spherical field like what required for previous variant embodiments.

Delays can be defined by simply providing inductances connecting the input of one section to the input of the immediately adjacent or following section with reference to the order of the excitation sequence. The inductances denoted by L1, L2, L3 in FIG. 10 are defined such that excitation delays provide an overall radiation field that is spherical or as much similar as possible to a spherical one and they can be integrated into electric or electronic circuitry provided for connection lines of the individual transducers inside an ultrasound probe or on the printed circuit board providing conductive tracks connecting the individual transducers of the transducer array to the termination connecting the multichannel cable.

Figure 11:
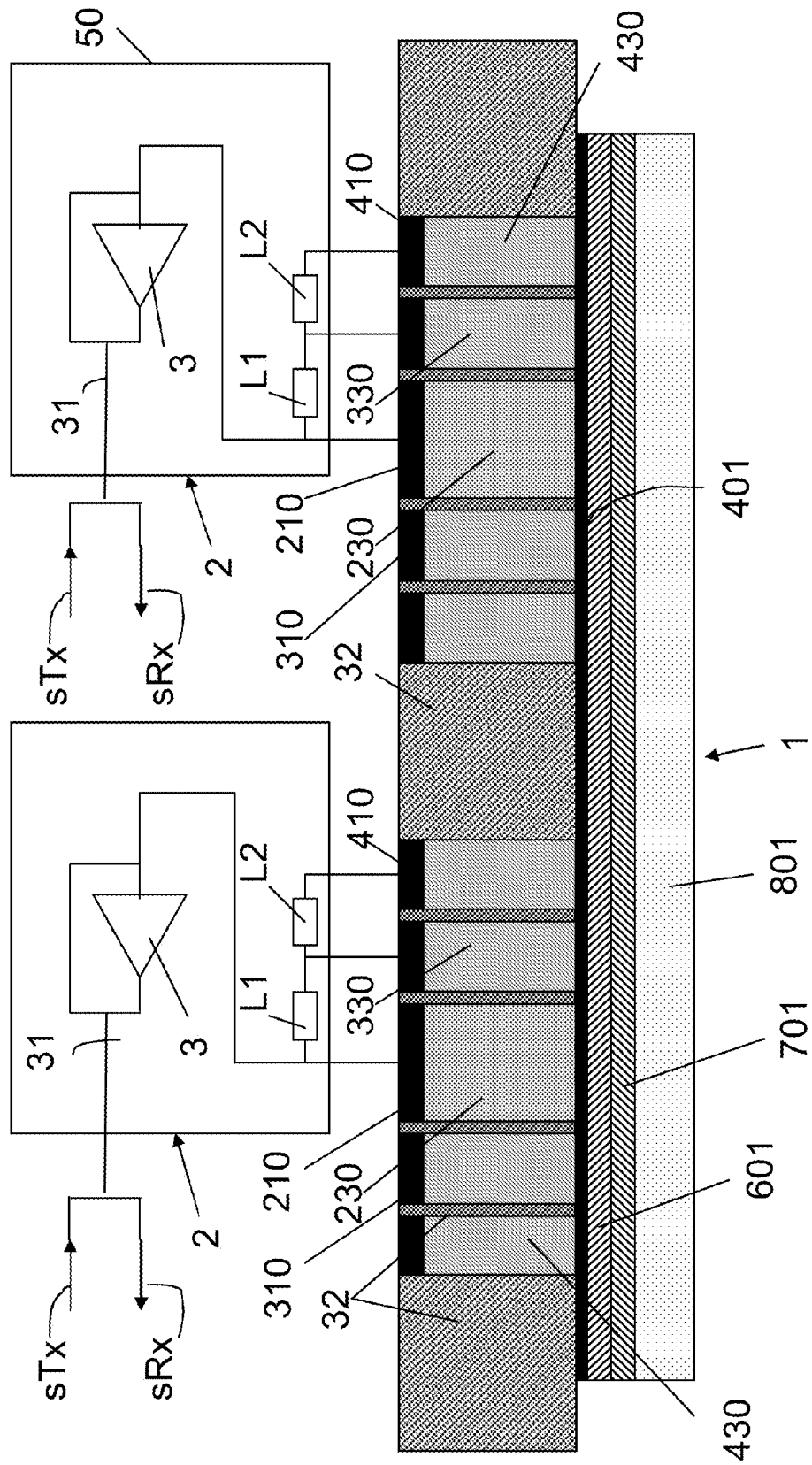
FIG. 11 is a cross-sectional view of a transducer array wherein transducers are made according to the principle of the second embodiment shown in FIG. 10.

FIG. 11 shows in greater detail an example of the construction of transducer elements and of the transducer array according to such an embodiment.

As it is clear in FIG. 11, the contact electrodes 10 forming the array 101 of contact electrodes and each one of them overlapping under electric contact a transducer element 30 by being congruent by the contact surface with said transducer element are divided into sections 210, 310, 410. In FIG. 11, each transducer element is divided into three concentric sections as illustrated in FIG. 10. According to the depicted embodiment, the shape of the sections is circular. Therefore each contact electrode 10 is also divided into three sections: a central plate 210 in contact and congruent with the contact surface of the central plate 230 of the transducer element; two concentric rings 310 and 410 each one is in contact with a concentric ring 330, 430 of the transducer element by being congruent with the contact surface of said ring 330, 430.

From each section 210, 310, 410 of the contact electrode a connection line comes out as, for example, a conductive track of a printed circuit board denoted by the schematic board 50 between said conductive tracks inductances L1 and L2 being connected by means of which each annular sections 310, 410 is connected to the connection line 31 for the transducer element. Such connection line in turn can be composed of a conductive track on a printed circuit board and on the printed circuit board preamplifiers of the reception signal can be bonded for each connection line 31 of each transducer element 30.

For the person skilled in the art it is clear that there is nearly perfect symmetry between the excitation signals transmitted to transducer elements and the reception signals generated by transducer elements excited by acoustic pulses. In this case, the acoustic pulse impinging on the transducer element causes each section 230, 330, 430 to generate a component of the reception signal for the portion of the acoustic signal detected there from and the components of the reception signal generated by the individual sections are summed together according to a time sequence providing predetermined delays for each component and with an order starting from the most central section towards the outermost sections in a way like delays of the excitation signal.

Figure 12:
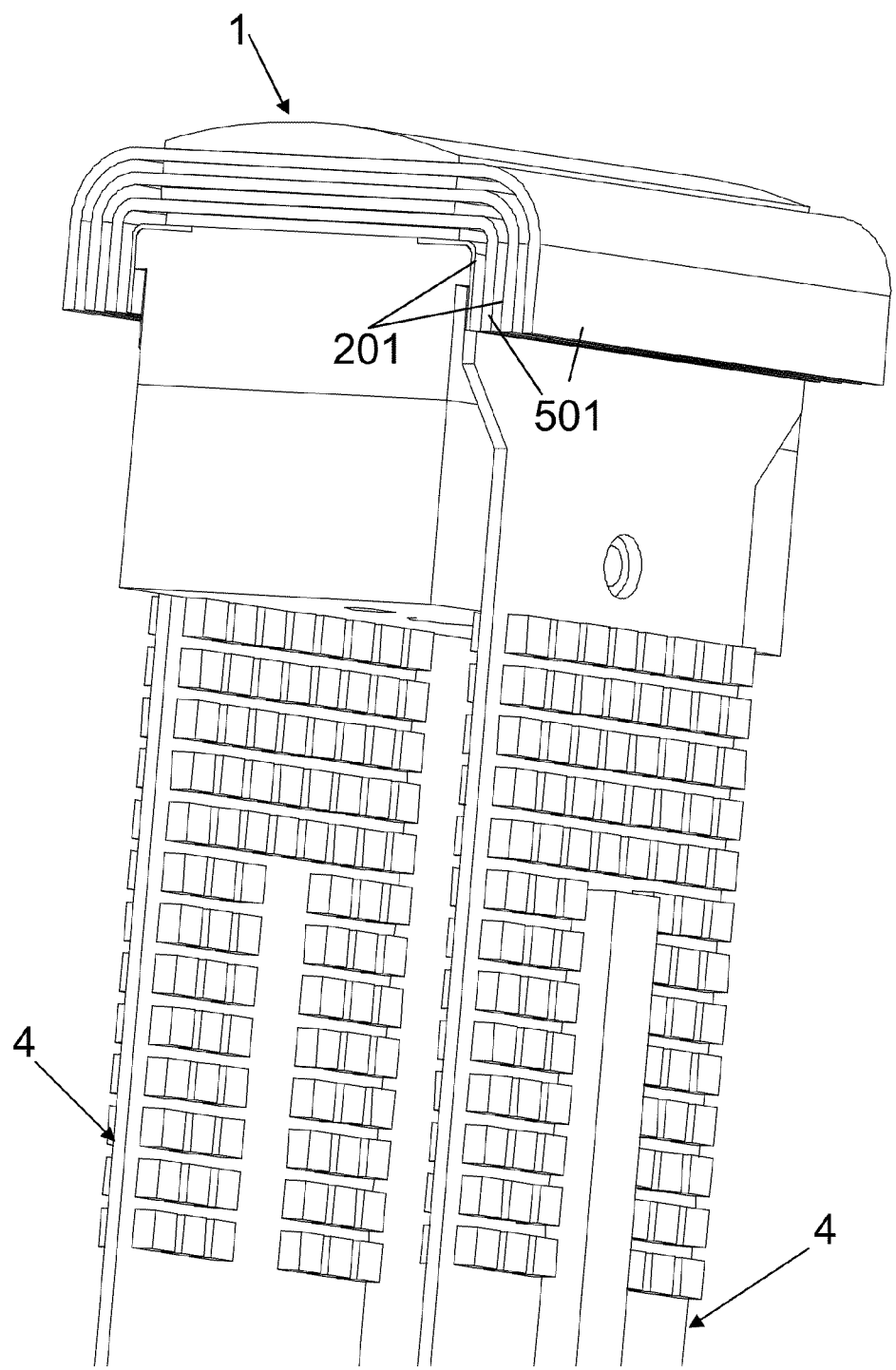
FIG. 12 is the construction of an ultrasound probe having a circuit processing electric excitation and reception signals integrated within the probe casing and allowing inductances for the delay of the components of the excitation and/or receiving signal one with respect to the other of sub-elements of the individual transducer elements to be easily mounted.

FIG. 12 shows an embodiment wherein the emitting/receiving head of the type described hereinbefore for an ultrasound probe is connected by means of terminations 201, 501 to printed circuit boards provided inside the casing of the ultrasound probe and denoted by 4 upon which both electronic circuits and delay inductances can be also provided. A more detailed description of the configuration is disclosed in EP 1681019 to the same applicant, which is incorporated by reference in its entirety.

In FIG. 12, it is important to note the possibility of providing a considerable space inside the probe for mounting electric or electronic components and therefore a variant embodiment can provide means for varying feeding delays of the excitation signal to the individual sections 230, 330, 430, 530 of a transducer element or to be applied to the components of the reception signals received from the individual sections 230, 330, 430, 530 in a way corresponding to the order defined by the sequence of excitation or reception delays. Such means can be of the electronic type, i.e. they can lead to a variation by control pulses or they can be of the mechanical type, i.e. can provide different delay inductances that can be alternatively connected to the circuit one in place of the other.

This solution advantageously would allow the emitting/receiving characteristics of the individual transducer elements to be adapted to the requirements of the desired application.

Finally, it is also noted that the circular shape may be advantageous due to the symmetry; however, the individual transducers can alternatively have a square, rectangular, rhomboidal or polygonal shape, and the different concentric sections being shaped according to the plan shape of the transducer element. Thus, for example, instead of concentric circular sections, square transducer elements can be divided into concentric square sections and the more generally polygonal ones can be divided into concentric polygonal sections always obtaining the desired defocusing effects.

Figure 13:
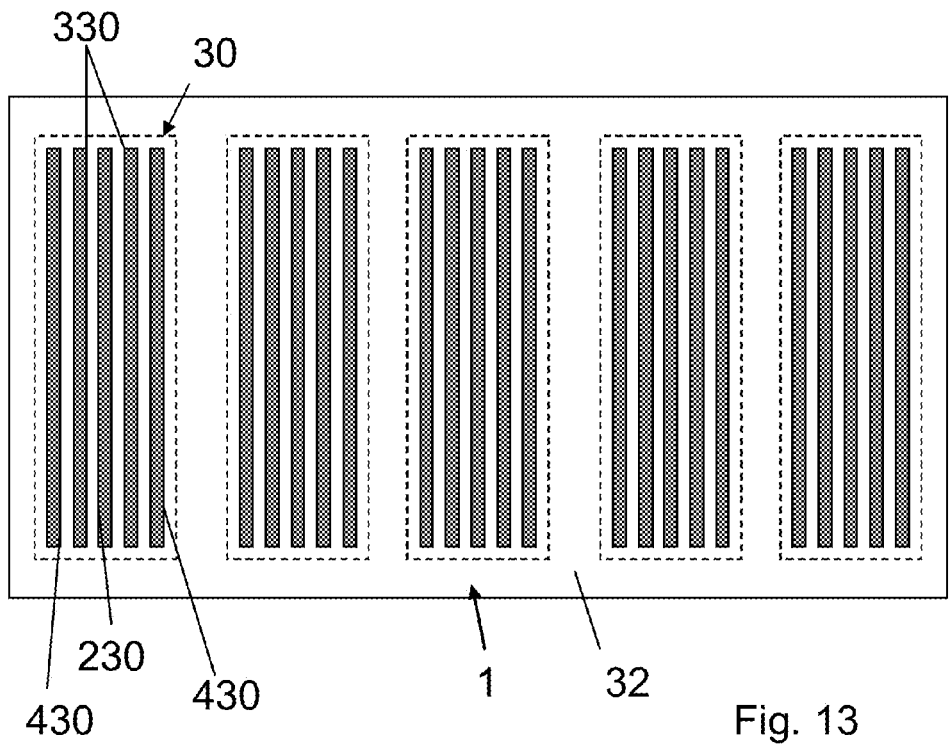
FIG. 13 is a schematic top plan view of a linear array of transducer elements wherein transducer elements are put side by side in a single row having a predetermined length, like reference numbers as in previous figures being provided for like parts or for parts having like functions.
Figure 14:
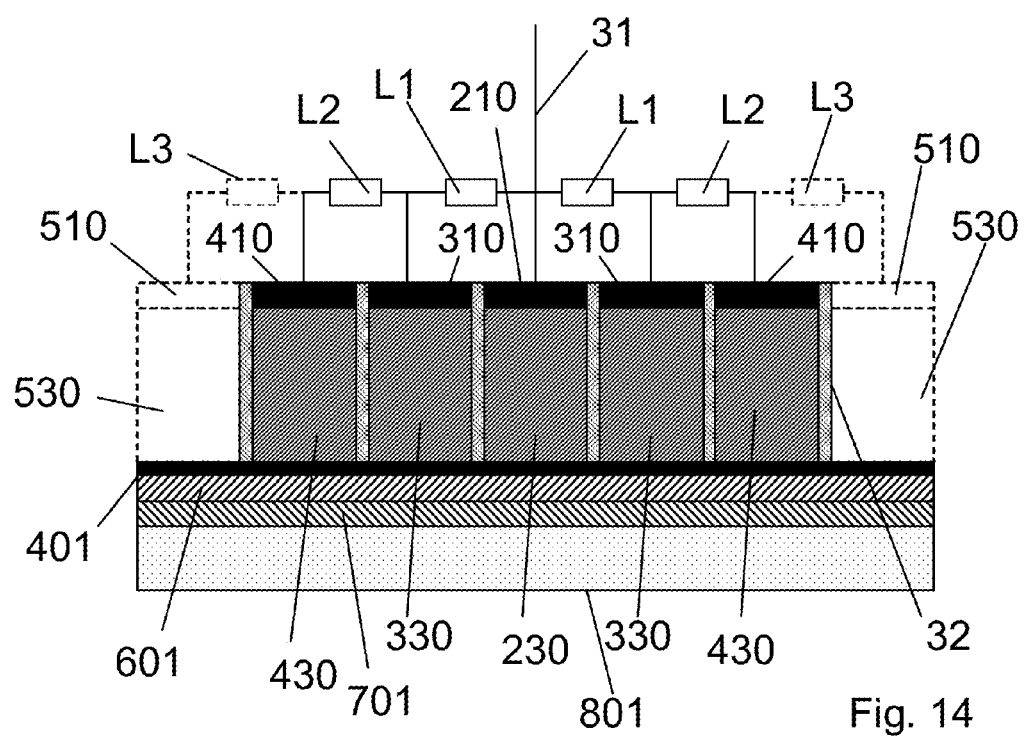
FIG. 14 is a schematic view relating to the embodiment of FIG. 13.

FIGS. 13 and 14 show a further embodiment wherein the array of transducer elements is of the linear type, i.e. wherein transducer elements are put side by side in only one row having a predetermined extension. FIGS. 13 and 14 have like reference numbers as in previous figures for like parts or for parts having a similar function. In this case, the array of transducers has an aperture corresponding to the length of the row. Transducer elements 30 can have rectangular emitting surfaces having the shortest side parallel to the length of the row of the adjacent transducer elements, the elements being arranged side by side along the longest sides thereof and the longest sides of the transducer elements being parallel to the width dimension of the transducer row.

The embodiment depicted in FIGS. 13 and 14 particularly relate to the embodiment of FIGS. 10 to 12. The embodiments of FIGS. 4 to 9 may also be applied wherein the array of transducer elements is of the linear type or composed of rectangular transducer elements. In this case defocusing means 40, 40' can be composed of concave or convex elements, whose concavity or convexity has a radius of curvature according to only one axis, which, in one embodiment, is coincident with the longitudinal axis of the corresponding element. Therefore, considering FIGS. 4 to 9 as sections along planes perpendicular to the surface of the array of transducer elements and perpendicular to the longitudinal axis of the transducer elements or to the axis according to which the curvature of the defocusing means is made these represent a further embodiment.

The embodiment of FIGS. 13 and 14 show how applying the solution providing individual transducer elements to be divided into sections to rectangular transducer elements particularly in a linear transducer array. In this case, each transducer element 30 is divided into several adjacent thin strips 230, 330, 430 and 210, 310, 410 both as regards the piezoelectric element and as regards the contact electrode 10. It is possible to provide any number of sections constituting the transducer element, such as denoted by the element 530 in FIG. 13 which is shown with broken lines. Advantageously in order to have an adaptation to the cylindrical axial symmetry, as for the concentric shape of FIGS. 10 to 12, it has been preferred to provide a central section 230, 210 and to provide symmetrically thereto pairs of laterally adjacent sections 330, 310, 430, 410 respectively to which delays are applied both for the emission and reception which are identical for each pair of sections 330, 310, 430, 410.

This can be clearly seen in the figures by providing the same reference numbers for delays inductances denoted by L1, L2, and L3.

Thus like the embodiment of FIGS. 10 to 12 by applying predetermined delays both in the excitation step and in the receiving step to each pair of sections equidistant from the central section than the other pairs it is possible to generate any acoustic field and particularly a cylindrical one or as much similar as possible to a cylindrical field.

With reference to the previous description it has to be noted that transducer elements can be of any type, for example piezoelectric ceramic ones, composites ones (i.e. with piezoelectric ceramic diced into microelements separated by resin in order to reduce the acoustic impedance), of the single-crystal type (i.e. made by a growth of piezoelectric material), or C-Mut type and therefore when the description refers to a transducer element as its specific piezoelectric element form characteristics provided in combination with said piezoelectric element can be provided in combination with any specific constructional form of said transducer element.

While the invention has been illustrated and described in detail in the drawings and foregoing description, the same is to be considered as illustrative and not restrictive in character, it being understood that only the preferred embodiments have been shown and described and that all changes and modifications that come within the spirit of the invention are desired to be protected. It is also contemplated that structures and features embodied in the present examples can be altered, rearranged, substituted, deleted, duplicated, combined, or added to each other. The articles "the", "a" and "an" are not necessarily limited to mean only one, but rather are inclusive and open ended so as to include, optionally, multiple such elements. All publications, patents, and patent applications cited in this specification are herein incorporated by reference as if each individual publication, patent, or patent application were specifically and individually indicated to be incorporated by reference and set forth in its entirety herein.

What is claimed is:

1. An electroacoustic transducer assembly for emitting and receiving acoustic radiation beams, the assembly comprising:
   an array of electroacoustic transducers composed of a plurality of individual transducer elements each one being made of an electroacoustic element;
   a contact electrode associated with each transducer element, the contact electrodes are constructed and arranged to input an excitation signal to excite the transducer element corresponding to the emission of an acoustic signal and to receive an electric reception signal corresponding to an acoustic signal impinging on the corresponding transducer element;
   a connection line connected to each contact electrode, the connection line is constructed and arranged to transmit/receive the electric excitation signal or the electric reception signal, respectively;
   a ground electrode connected to each transducer element, the transducer elements are supported by an acoustically and electrically insulating material into which the transducer elements are at least partially embedded; and
   a plurality of defocusing elements, there being a separate defocusing element associated with each transducer element of said plurality, each defocusing element is constructed and arranged for defocusing a radiation pulse emitted from its corresponding transducer element to cause the radiation pulse to generate a substantially cylindrical or spherical acoustic field.

2. The assembly of claim 1, wherein said defocusing element is provided on the side of the transducer emitting the radiation pulse, the defocusing element having a first surface facing the transducer element and a second surface opposite of the first surface.

3. The assembly of claim 2, wherein the second surface of the defocusing element has a convex shape, the defocusing element is made of a material constructed an arranged to propagate acoustic radiation at a high velocity.

4. The assembly of claim 2, wherein the second surface of the defocusing element has a concave shape, the defocusing element is made of a material constructed an arranged to propagate acoustic radiation at a low velocity.

5. The assembly of claim 2, wherein each transducer element is constructed and arranged with a plurality of transducer element sections, said transducer element sections are acoustically and electrically insulated one with respect to the other, the transducer element sections are each electrically connected to a corresponding excitation signal, the excitation signal to each transducer element section has a predetermined time delay for the different sections constituting the transducer element relative to each other and according to an excitation order defined by a predetermined time sequence.

6. The assembly of claim 5, wherein each contact electrode is divided into a plurality of electrode sections whose number size and shape substantially correspond to the transducer element sections, each electrode section has a dedicated connection line electrically connected to a main connection line by a delay means.

7. The assembly of claim 5, wherein each transducer element section has a rectangular shape, the transducer element sections are constructed and arranged side-by-side along their long sides.

8. The assembly of claim 5, wherein each transducer element section has a circular shape and the transducer element sections are concentrically arranged.

9. The assembly of claim 5, wherein the time sequence for exciting the transducer element sections is such that a central transducer element section is the first to be excited and then the transducer element sections equidistant from the central one are progressively and sequentially excited.

10. The assembly of claim 6, wherein the delay means is a delay inductance located on the dedicated connection line.

11. The assembly of claim 5, wherein each transducer element comprises a contact electrode which is composed of concentric electrode sections and a piezoelectric element overlapped to said contact electrode, the plurality of transducer element sections are separated from one another, each of the transducer element sections is in electrical contact with a congruent electrode section and overlaps the same, each electrode section is electrically connected to an adjacent electrode section by an inductance and an input line for the excitation signal is connected to a central electrode.

12. The assembly of claim 11, wherein the inductances act on the components of the reception signal.

13. The assembly of claim 1, wherein each transducer element is divided into different sections constructed and arranged to be excited separately one with respect to the other, reception signals are collected separately one with respect to the other and then are combined, the defocusing element is provided on the emitting surface of the transducer element, and wherein the defocusing element is an acoustic lens distributing the acoustic radiation on an acoustic field having a predetermined shape.

14. An ultrasound probe comprising:
a casing enclosing a head constructed and arranged for transmitting/receiving acoustic radiation beams or pulses, the head comprising an array of electroacoustic transducers composed of a plurality of individual transducer elements each one being made of an electroacoustic element;
a contact electrode associated with each transducer element, the contact electrodes are constructed and arranged to input an excitation signal to excite the transducer element corresponding to the emission of an acoustic signal and to receive an electric reception signal corresponding to an acoustic signal impinging on the corresponding transducer element;
a connection line connected to each contact electrode, the connection line is constructed and arranged to transmit/receive the electric excitation signal or the electric reception signal, respectively;
a ground electrode connected to each transducer element, the transducer elements are supported by an acoustically and electrically insulating material into which the transducer elements are at least partially embedded; and
a plurality of defocusing elements, there being a separate defocusing element associated with each transducer element of said plurality, each defocusing element is constructed and arranged for defocusing a radiation pulse emitted from its corresponding transducer element to cause the radiation pulse to generate a substantially cylindrical or spherical acoustic field.

15. The probe of claim 14, wherein said defocusing element is provided on the side of the transducer emitting the radiation pulse, the defocusing element having a first surface facing the transducer element and a second surface opposite of the first surface.

16. The probe of claim 15, wherein the second surface of the defocusing element has a convex shape, the defocusing element is made of a material constructed an arranged to propagate acoustic radiation at a high velocity.

17. The probe of claim 15, wherein the second surface of the defocusing element has a concave shape, the defocusing element is made of a material constructed an arranged to propagate acoustic radiation at a low velocity.

18. The probe of claim 15, wherein each transducer element is constructed and arranged with a plurality of transducer element sections, said transducer element sections are acoustically and electrically insulated one with respect to the other, the transducer element sections are each electrically connected to a corresponding excitation signal, the excitation signal to each transducer element section has a predetermined time delay for the different sections constituting the transducer element relative to each other and according to an excitation order defined by a predetermined time sequence.

19. The probe of claim 18, wherein each contact electrode is divided into a plurality of electrode sections whose number, size and shape substantially correspond to the transducer element sections, each electrode section has a dedicated connection line electrically connected to a main connection line by a delay means.

20. The probe of claim 18, wherein each transducer element section has a rectangular shape, the transducer element sections are constructed and arranged side-by-side along their long sides.

21. The probe of claim 18, wherein each transducer element section has a circular shape and the transducer element sections are concentrically arranged.

22. The probe of claim 18, wherein the time sequence for exciting the transducer element sections is such that a central transducer element section is the first to be excited and then the transducer element sections equidistant from the central one are progressively and sequentially excited.

23. The probe of claim 19, wherein the delay means is a delay inductance located on the dedicated connection line.

24. The probe of claim 18, wherein each transducer element comprises a contact electrode which is composed of concentric electrode sections and a piezoelectric element overlapped to said contact electrode, the plurality of transducer element sections are separated from one another, each of the transducer element sections is in electrical contact with a congruent electrode section and overlaps the same, each electrode section is electrically connected to an adjacent electrode section by an inductance and an input line for the excitation signal is connected to a central electrode.

25. The probe of claim 24, wherein the inductances act on the components of the reception signal.

26. The probe of claim 14, wherein each transducer element is divided into different sections constructed and arranged to be excited separately one with respect to the other, reception signals are collected separately one with respect to the other and then are combined, the defocusing element is provided on the emitting surface of the transducer element, the defocusing element is an acoustic lens distributing the acoustic radiation on an acoustic field having a predetermined shape.

27. An electroacoustic transducer assembly for emitting and receiving acoustic radiation beams, the assembly comprising:
   an array of electroacoustic transducers composed of a plurality of individual transducer elements each one being made of an electroacoustic element;
   a contact electrode associated with each transducer element, the contact electrodes are constructed and arranged to input an excitation signal to excite the transducer element corresponding to the emission of an acoustic signal and to receive an electric reception signal corresponding to an acoustic signal impinging on the corresponding transducer element;
   a connection line connected to each contact electrode, the connection line is constructed and arranged to transmit/receive the electric excitation signal or the electric reception signal, respectively;
   a ground electrode connected to each transducer element, the transducer elements are supported by an acoustically and electrically insulating material into which the transducer elements are at least partially embedded;
   a plurality of defocusing elements, there being a separate defocusing element associated with each transducer element of said plurality, each defocusing element is constructed and arranged for defocusing a radiation pulse emitted from its corresponding transducer element to cause the radiation pulse to generate a substantially cylindrical or spherical acoustic field; and
   wherein each transducer element is constructed and arranged with a plurality of transducer element sections, said transducer element sections are acoustically and electrically insulated one with respect to the other, the transducer element sections are each electrically connected to a corresponding excitation signal, the excitation signal to each transducer element section has a predetermined time delay for the different sections constituting the transducer element relative to each other and according to an excitation order defined by a predetermined time sequence.

28. The assembly of claim 27 wherein each transducer element comprises a contact electrode which is composed of concentric electrode sections and a piezoelectric element overlapped to said contact electrode, the plurality of transducer element sections are separated from one another, each of the transducer element sections is in electrical contact with a congruent electrode section and overlaps the same, each electrode section is electrically connected to an adjacent electrode section by an inductance and an input line for the excitation signal is connected to a central electrode.

29. The assembly of claim 28 wherein the inductances act on the components of the reception signal.

* * * * *